(12) United States Patent
Insley et al.

(10) Patent No.: US 6,514,412 B1
(45) Date of Patent: Feb. 4, 2003

(54) MICROSTRUCTURED SEPARATION DEVICE

(75) Inventors: Thomas I. Insley, West Lakeland Township, MN (US); Raymond P. Johnston, Lake Elmo, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/100,163

(22) Filed: Jun. 18, 1998

(51) Int. Cl.$^7$ .............................................. B01D 61/00
(52) U.S. Cl. .................. 210/649; 210/486; 210/321.75; 210/321.84; 210/321.83; 210/321.85; 210/416.1; 210/644
(58) Field of Search ........................... 210/486, 321.75, 210/321.76, 321.84, 321.85, 321.83, 498, 416.1, 649, 644

(56) References Cited

U.S. PATENT DOCUMENTS

| | | | |
|---|---|---|---|
| 3,401,798 A | * | 9/1968 | Nirop |
| 3,417,870 A | * | 12/1968 | Bray ...................... 210/321.83 |
| 3,511,381 A | * | 5/1970 | Alwall et al. .......... 210/321.75 |
| 3,753,712 A | | 8/1973 | Janneck et al. |
| 3,813,334 A | * | 5/1974 | Bray ...................... 210/321.83 |
| 4,392,362 A | | 7/1983 | Little |
| 4,413,407 A | | 11/1983 | Columbus |
| 4,579,555 A | | 4/1986 | Russo |
| 4,601,861 A | | 7/1986 | Pricone et al. |
| 4,639,748 A | | 1/1987 | Drake et al. |
| 4,756,835 A | * | 7/1988 | Wilson |
| 4,758,481 A | | 7/1988 | Fauvel |
| 4,913,858 A | | 4/1990 | Miekka et al. |
| 5,152,060 A | | 10/1992 | Schubert et al. |
| 5,176,667 A | | 1/1993 | DeBring |
| 5,232,589 A | * | 8/1993 | Kopf |
| 5,376,252 A | | 12/1994 | Ekström et al. |
| 5,411,858 A | | 5/1995 | McGeehan et al. |
| 5,514,120 A | | 5/1996 | Johnston et al. |
| 5,562,825 A | * | 10/1996 | Yamada et al. |
| 5,601,678 A | | 2/1997 | Gerber et al. |
| 5,651,889 A | * | 7/1997 | Wataya et al. |
| 5,703,633 A | | 12/1997 | Gehrer et al. |
| 6,277,282 B1 | * | 8/2001 | Kihara et al. |
| 6,290,685 B1 | * | 9/2001 | Insley et al. |

FOREIGN PATENT DOCUMENTS

| | | | |
|---|---|---|---|
| DE | 32 12 295 A1 | | 10/1983 |
| DE | 195 01 017 A1 | | 7/1996 |
| EP | 0 039 291 A1 | | 11/1981 |
| EP | 0 329 340 A2 | | 8/1989 |
| GB | 1 338 579 | | 11/1973 |
| GB | 1 354 502 | | 5/1974 |
| WO | 9609879 | * | 4/1996 |
| WO | 97/02357 | | 1/1997 |
| WO | 97/13633 | | 4/1997 |
| WO | 98/00231 | | 1/1998 |
| WO | 98/24544 | | 6/1998 |

* cited by examiner

*Primary Examiner*—Ana Fortuna
(74) *Attorney, Agent, or Firm*—Karl G. Hanson; Christopher D. Gram; Robert W. Sprague

(57) ABSTRACT

An active fluid separation device for removing a constituent of a fluid mixture. The separation device formed from a first polymeric structured layer having a plurality of flow channels defined in one surface, and a selectively permeable fluid separation media covering at least some of the flow channels. An external source is also included to provide a potential over the flow channels to promote movement of the fluid through the separation media, thereby removing a constituent component of the fluid mixture. A manifold in fluid contact with the flow channels of the structured layer may also be used to operatively permit the source to provide the potential over the flow channels.

19 Claims, 8 Drawing Sheets

MICROSTRUCTURED SEPARATION DEVICE

The present invention relates to a separation device comprising a selectively permeable separation medium bonded to a microstructured film that is used in connection with a source for driving a fluid mixture through the device.

BACKGROUND

Fluid separation devices remove a constituent from a fluid mixture by passing the fluid mixture through a selectively permeable separation medium. The undesirable component (s) of the fluid mixture remain on one side of the separation medium, and the filtrate passes through to the other side of the separation medium. Types of separations available with such devices include gas-solid, gas-gas, gas-liquid, liquid-liquid, and liquid-solid. Applications using these types of separations include water desalinization, dialysis, microfiltration to remove bacteria and other fine particles, detoxification of industrial waste, sewage treatment, and ultrafiltration to remove very fine or dissolved solids from liquids or gases. Typically, these fluid separation devices are at least partially submersed or flooded within the fluid mixture during the separation process.

Transport and control of a fluid mixture through a selectively permeable separation medium may be achieved in a separation system by a fluid transport mechanism independent of the separation medium. An example of this type of system includes a pumping system wherein the fluid mixture is pumped from one tank through a separation medium into another tank. On the other hand, transport and control of the fluid mixture may be achieved as part of a separation device, wherein a separation medium is coupled to a fluid transport mechanism. For example, the separation device may include a vacuum distribution mechanism coupled to a separation medium for driving the fluid mixture through the separation medium by a vacuum source.

The transport of fluid by a conduit or other device may be characterized based on the mechanism that causes flow within the conduit or device. Where fluid transport pertains to a nonspontaneous fluid flow regime wherein the fluid flow results, for the most part, from an external force applied to the device, such fluid transport mechanism is considered active. On the other hand, where the fluid transport pertains to a spontaneous flow regime wherein the fluid movement stems from a property inherent to the transport device, such fluid transport mechanism is considered passive. A catheter is a well-known example of an active fluid transport device. Typically, catheters that are used in the medical field to drain fluid from a body cavity are connected to a vacuum source to draw the liquid through the device. A passive fluid transport device is an absorbent pad.

Active fluid transport products have been developed based upon specific applications, including absorbent pads or a liquid pervious layer combined with fluid transport devices. For example, mat products including active fluid transport and absorbent pads or liquid pervious layers are described in U.S. Pat. No. 5,437,651 to Todd et al., and U.S. Pat. No. 5,349,965 to McCarver. In each case, channels are defined on a surface of a substrate to direct liquid flow from substantially all of the area of a liquid pervious layer. These products remove liquid while having the liquid pervious layer act as a liquid absorbing and storing layer and/or to define a liquid receiving chamber. In Todd et al., a flexible backing plate is attached to an absorbent portion, and a suction source is applied to the backing plate. The backing plate comprises a plurality of channels for directing the vacuum provided by the suction source more evenly across the surface of the absorbent portion. In McCarver, a flexible pad or suction rail having a liquid permeable top surface and a liquid impermeable bottom surface is connected to a vacuum source. The suction draws liquid down into a liquid receiving chamber as it passes through the liquid pervious layer, and draws the accumulated liquid away. The liquid receiving chamber contains separation means dividing the chamber into channels for keeping the chamber from collapsing when the chamber is placed under a negative pressure.

Another flexible fluid transport product has been recently introduced and is commercially available under the tradename "Fluid Control" floor suction mat, from Technol Medical Products Inc. This product is used to absorb fluids that fall from a surgical site during a surgical procedure. The device has an absorbent mat that resides above a multitude of parallel enclosed channels. Holes are provided in the channel surfaces that interface with the absorbent mat so that fluid recovered by the mat can be drawn into the channels. The parallel channels are connected to a manifold for attachment with suction tubing. Thus, after fluid has accumulated within the mat, removal thereof can be facilitated through the multiple channels by the application of vacuum.

Examples of flexible fluid transport devices that utilize both active and passive fluid transport are described in U.S. Pat. No. 3,520,300 to Flower, U.S. Pat. No. 4,747,166 to Kuntz, and U.S. Pat. No. 5,628,735 to Skow. In Flower, a surgical sponge and suction device is disclosed having an absorbent material over a perforated wall of a chamber that is connected to a vacuum source via a tube. In Kuntz, a pad, having an absorbent core encased in hydrophobic material but with a perforated top surface, surrounds a perforated tube coupled to a vacuum source. In Skow, a mat is provided comprising a material having a high wicking property, and within the material, a flexible suction tube is provided for preventing the mat from becoming saturated with fluid. In all three cases, the tubing limits where the fluid is evacuated from within the device.

Examples of other channeled mats for fluid removal are shown in U.S. Pat. No. 4,533,352 to Van Beek et al. and U.S. Pat. No. 4,679,590 to Hergenroeder; however, these mats provide structure for receiving fluid without defining a receiving chamber closed by a liquid pervious layer. Van Beek et al. shows a ribbed mat with a centrally located suction hose connected to the ribs by openings in the hose. Hergenroeder shows a mat having a gridwork of small basins forming a collection surface that are drained into channels connected to a suction source.

Examples of passive fluid transport devices having channeled fluid transport structures are described in PCT International Publication No. WO 93/11727, entitled "Liquid Management Member For Absorbent Articles." Disclosed is the use of a liquid management member having a microstructure-bearing hydrophilic surface, preferably in combination with a liquid permeable top sheet, a back sheet, and an absorbent core disposed between the top and back sheets. The liquid management member promotes rapid directional spreading of liquids and is in contact with the absorbent core.

Specific examples of fluid separation devices include the type disclosed in U.S. Pat. No. 5,455,771 to Degen. In the Degen patent, a collection of fine, hollow, permeable or semi-permeable fiber strands are used as a fluid transport device. These hollow fibers may filter a fluid by passing it over the exterior of the fibers and/or by passing the fluid through the fiber walls and into the interior of the fibers. Problems associated with these types of separation devices include problems with the production of the fibers. Moreover, hollow fiber separation devices are limited in application and susceptible to a number of problems. Fiber fragility and the general difficulty of handling bundles of small individual elements hampers their use. High unit cost, fouling, and a lack of geometric (profile) flexibility further limit application of these fibers as a fluid transport mechanism in separation devices. The inability to practically distribute long lengths and large numbers of hollow fibers into useful transport arrays makes their use inappropriate for all but a limited range of active fluid transport applications.

SUMMARY OF THE INVENTION

The present invention overcomes the disadvantages and shortcomings of the prior art by providing a separation device that is flexible, efficient, easy to handle and use, inexpensive to manufacture, and extremely versatile and adaptable to various separation applications. More specifically, the present invention provides a separation device comprising a separation module formed from a structured layer having a plurality of flow channels and a separation media, as well as a source providing a potential across the flow channels of the structured layer to drive a fluid mixture through the separation media in order to remove a constituent(s) from the fluid mixture.

The separation module preferably includes a manifold connected in fluid contact with the flow channels of the structured surface. The manifold may be connected to the source, or may be connected to a receptacle or to another device. The source provided as part of the separation device may connect to the manifold, or may connect to the separation module in some other manner. The source may be a vacuum that pulls a fluid mixture through the separation media, into the flow channels and out through the manifold, or it may pull a fluid mixture through the manifold, into the flow channels and across the separation media. Alternatively, the source may be a pressure source, such as a pump, that pushes the fluid mixture through the separation media in either direction discussed above.

The separation media comprises selectively permeable separation material, such as microporous film, microperforated film, nonwoven filtration web, or other types of filtration material. The separation module may be formed with a single layer of separation media, or it may have multiple layers that are all the same, or are different from one another, depending on the separation application.

The flow channels of the structured layer are defined by a series of peaks whose sidewalls may converge, or that may be separated by a planar floor. Alternatively, the peaks may be separated by at least one sub-peak forming sub-channels within each flow channel. The flow channels may vary across the structured surface, channel to channel, or within each channel. The structured surface may be formed from a polymer such as polytetrafluoroethylene or polypropylene, or other suitable material.

In another embodiment, the separation module may comprise more than one structured layer at least partially covered by a separation media. A manifold in fluid contact with the flow channels of the first layer would also be in fluid contact with the flow channels of at least one other layer.

The present invention also teaches a method of removing a constituent from a fluid mixture comprising the steps of providing a separation module of the present invention, connecting the module to an externally provided source to form the separation device, flooding the module within a fluid mixture to be filtered, and driving the fluid mixture through the module by the source, thereby removing a constituent(s) from the fluid mixture. This method may also encompass a source that is a vacuum or a source that is a pressure source. The method may drive the fluid mixture through a manifold into the flow channels of the structured layer and across the separation media, or it may drive fluid through the separation media into the flow channels and out through the manifold. The separation module of the method may have a single separation media layer, or it may include multiple separation media layers that are either the same or different from one another.

DETAILED DESCRIPTION OF PREFERRED EMBODIMENTS

Figure 1:
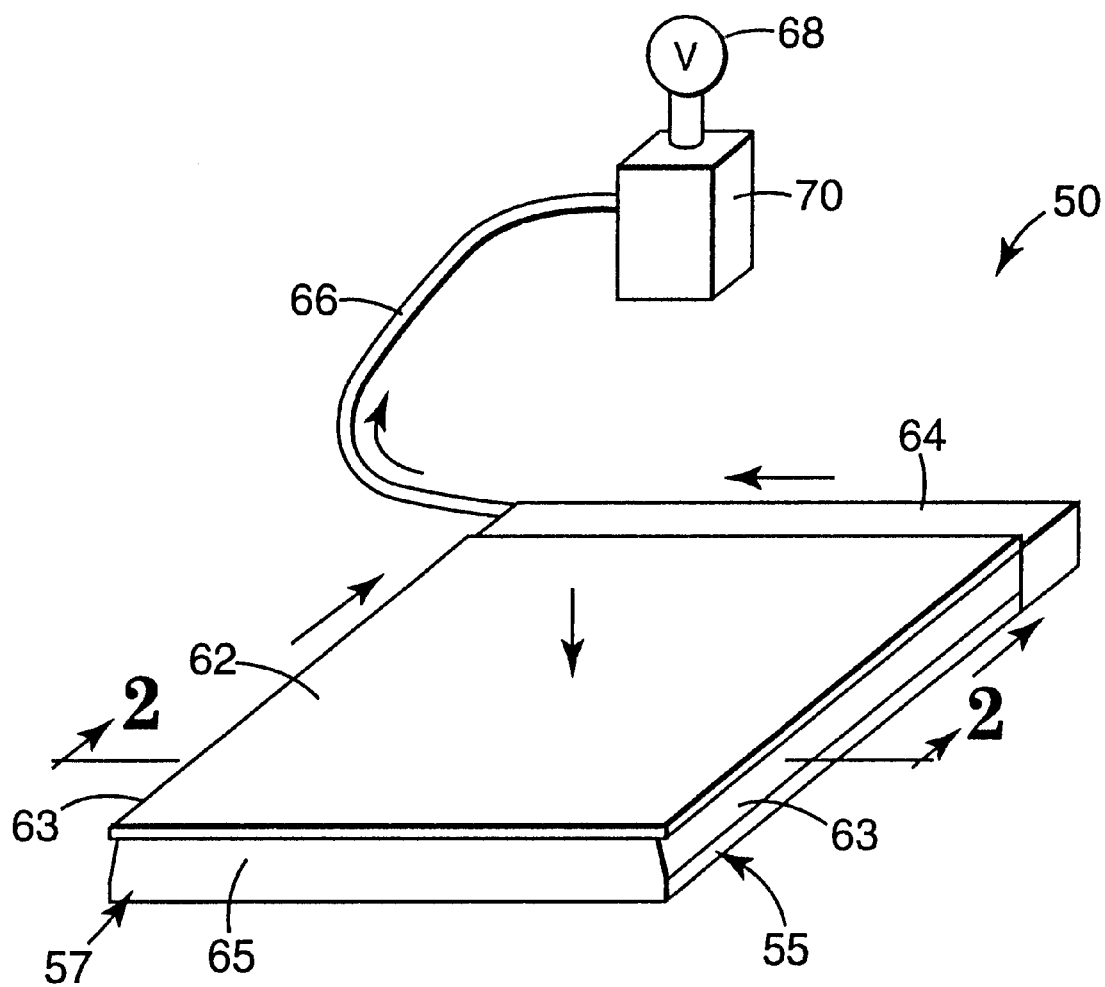
FIG. 1 is a perspective view of a separation device in accordance with the present invention using a vacuum source to drive a fluid mixture.
Figure 2:
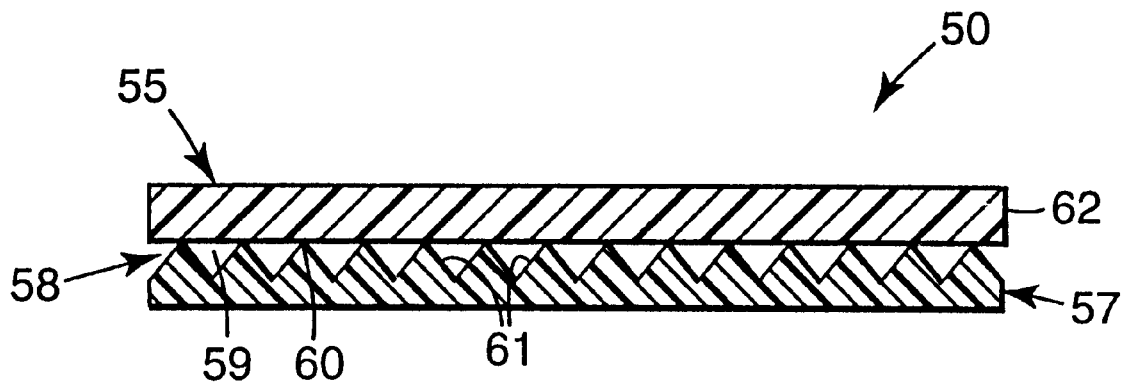
FIG. 2 is a cross-sectional view taken along line 2—2 of the separation device of FIG. 1.

With reference to the attached Figures, like components are labeled with like numerals throughout the several Figures. FIGS. 1 and 2 illustrate a separation device 50 in accordance with the present invention. FIG. 2 is a cross sectional view of the separation device 50 taken along line 2—2 of FIG. 1. The separation device 50 basically includes a separation module 55 connected to a source 68. The separation module 55 has a structured layer 57 having a structured surface 58 on one of its two major surfaces. The structured surface 58 comprises a plurality of channels 59 formed within the layer 57, preferably as shown in a consistent, ordered manner. Each channel 59 need not be the same as another of the layer 57, but the channels 59 are preferably ordered in the sense that each channel 59 is set by a predetermined design of the structured surface 58 of layer 57.

The layer 57 may comprise flexible, semi-rigid, or rigid material, which may be chosen depending on the particular application of the separation device 50. Preferably, the layer 57 comprises a polymeric material because such material is typically less expensive and because such polymeric material can be accurately formed with a structured surface 58. Moreover, by the use of a polymeric layer 57 in the form of, for example, a film layer can provide a structured surface defining a large number of and high density of fluid flow channels 59 on a major surface thereof. Thus, a highly efficient, inexpensive separation device of the present invention is amenable to being manufactured with a high level of accuracy and economy. Polymeric materials may be chosen, for example, based on flexibility, rigidity, permeability, etc.

As shown in FIG. 2, the channels 59 of layer 57 are defined by a series of peaks 60 formed of sidewalls 61. In some cases, it will be desirable to extend the peaks 60 entirely from one edge of the layer 57 to another; although, for other applications, it may be desirable to extend the peaks 60 only along a portion of the structured surface 58. That is, channels 59 that are defined between peaks 60 may extend entirely from one edge to another edge of the layer 57, or such channels 59 may only be defined to extend over a portion of the layer 57. One or more channel portions may begin from an edge of the layer 57, or may be entirely intermediately provided within the structured surface 58 of the layer 57.

The separation module 55 also includes a selectively permeable separation media 62 covering at least a portion of, but preferably all of, the structured layer 57. Each of the channels 59 may be, but need not be, closed off at one end and covered by the separation media 62 so that all of the fluid mixture that is run through the separation module 55 will pass through the separation media 62. Preferably, the separation media 62 is bonded or otherwise sealed to the structured layer 57 along the two sides 63 that are parallel to the channels 59, as well as along one end 65. The separation media 62 may also be bonded to the structured layer 57 at the peaks 60 of the channels 59, if desired.

Figure 3:
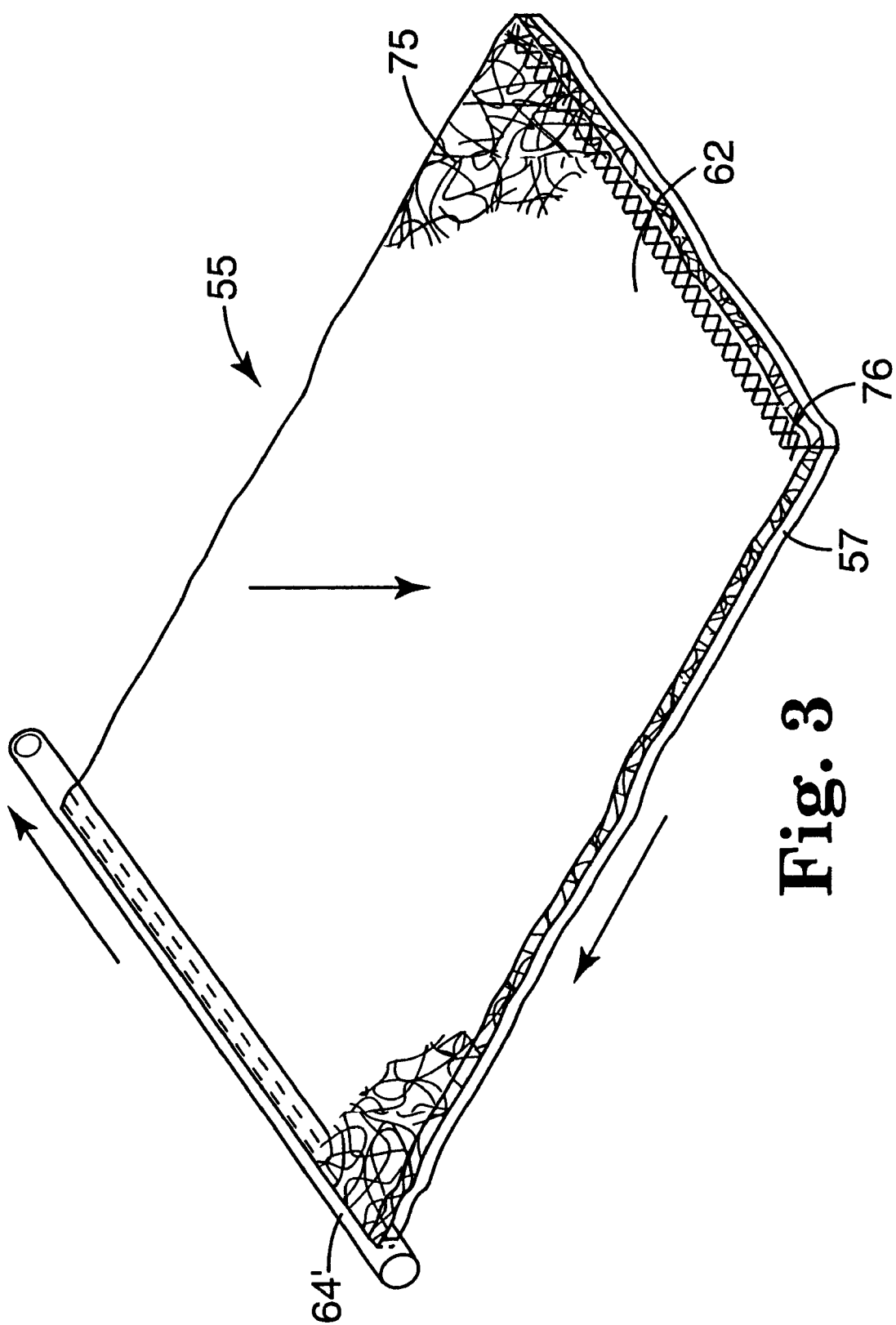
FIG. 3 is a perspective view of a separation module in accordance with the present invention having a nonwoven web for a separation media.

The selectively permeable separation media 62 can be chosen to remove desired constituents from a fluid mixture as the fluid mixture passes through the separation media 62. The separation media 62 may be any of a number of types of filtration media including, without limitation, microporous films, micro-perforated films, nonwoven webs, woven webs, microporous foams, a stacked microstructure filtration media as shown and described in commonly owned co-pending application Ser. No. 09/106,506, to Insley et al. filed on the same date as this case and entitled "Structured Surface Filtration Media", and the like. An embodiment of a separation module 55 of the present invention wherein the separation media 62 is a nonwoven web 75 sealed at one end 76, is shown in FIG. 3. Such a seal may be accomplished by head pressure sealing the edge of the nonwoven web 75 to an edge of the structured layer 57, in which case, the structured surface 58 at the edge may be crushed. Other adhesives or sealants could be used instead or in combination.

Figure 4:
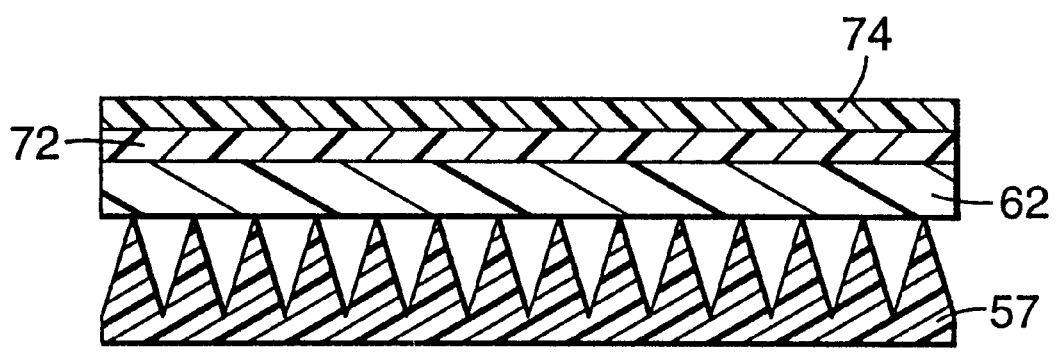
FIG. 4 is a cross-sectional view of a separation module in accordance with the present invention having multiple separation media layers.

The separation media 62 that is to be used for a given application will depend on the requirements of the separation, such as gas-solid, gas-liquid, liquid-solid, or liquid-liquid. Multiple layers of separation media 62, 72 and 74 may also be used in a given embodiment in order to meet the separation requirements of the application, as illustrated in FIG. 4. These separation media 62, 72 and 74 may all be the same, or may all be different, or may have some the same and some different, depending on what the requirements of the various separation media are, such as increased separation capacity and/or multiple constituent removal.

Alternatively, the separation media 62 may be removable and replaceable with respect to the separation module 55. By removably mounting the separation module 62, instead of permanent bonding or otherwise permanently sealing it, to the structured layer 58 the separation media 62 may be replaced by the same type of or a different type of separation media material. The separation module 55 may then be reused for another fluid separation process, or may continue to be used in the same process.

Figure 13:
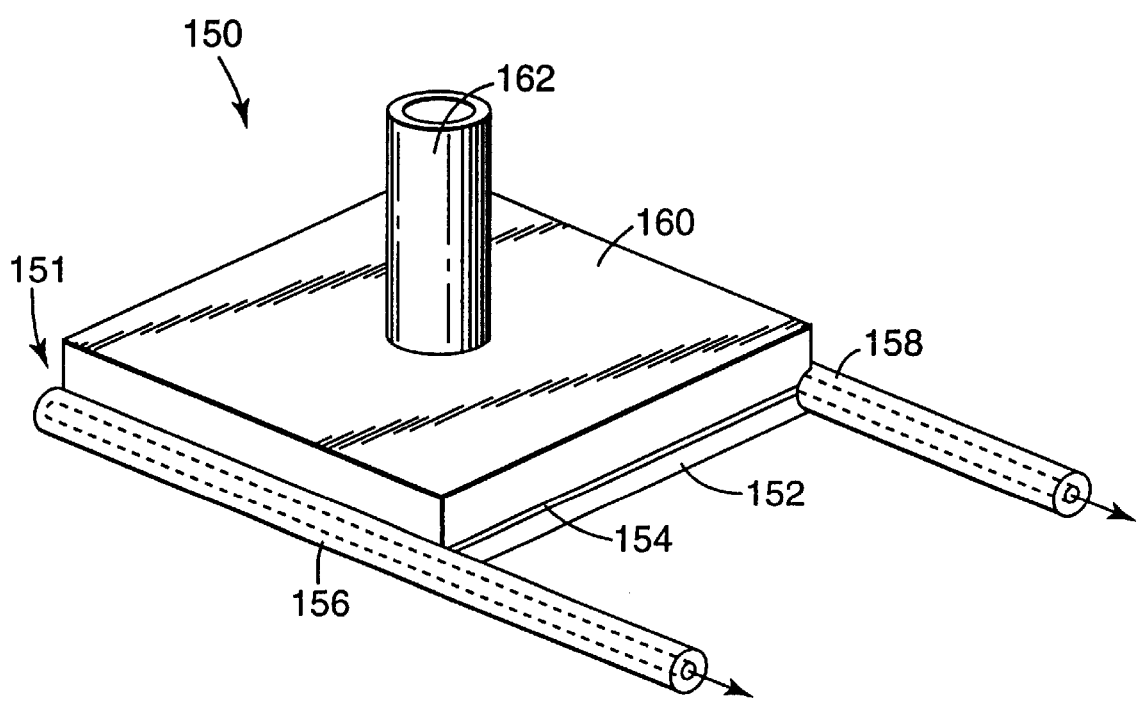
FIG. 13 is a perspective view of a separation device in accordance with the present invention using a pressure differential through a separation cover to drive a fluid mixture.

In addition, the separation module 55 also preferably includes a manifold 64 or 64' (See FIGS. 1 and 3, respectively) coupled to at least a plurality of the channels 59 of the structured layer 57, and preferably coupled, as shown in these embodiments, to the separation media 62 at a common side, so that a majority of the discrete flow channels 59 are in fluid contact with the manifold 64. The manifold 64 or 64' preferably is in fluid communication with each of the channels 59 through outlets (not shown) thereof, and is provided with a plenum (not shown) that is defined internally therein and which is in fluid communication with channels 59. The plenum may simply comprise a chamber within the manifold 64 that is sealingly connected to at least a plurality of the channels 59. The manifold 64 may be flexible, semi-rigid, or rigid, like the layer 57. Moreover, a second manifold or more may also be provided on the other side of layer 57, as illustrated in FIG. 13 (and discussed in detail below), depending on the particular application However, the manifold 64 may connect only to the channels 59 and not to the separation media by excluding the separation media from contact with the plenum, or by the addition of a impermeable cover layer bonded to the structured layer between the manifold and the separation media. This cover layer would then form flow passages in a portion of the structured layer where fluid is transported between a port open to the plenum and another port open to the separation media. The manifold may couple to the flow channels at the end of the structured layer, or it may couple to the flow channels on top of the structured surface, or in any other manner suitable for providing fluid contact between the manifold and the flow channels. Alternatively, the channels may connect to a central passage, such as those shown in FIGS. 7–9 (and discussed below), or they may connect directly to a source without the use of a manifold.

The separation device creates an active fluid flow that operates by a source 68 producing a potential over the flow channels 59. The potential source may comprise any means that provides a potential difference across a plurality of the flow channels 59 from a first potential to a second potential, except for gravitational forces alone. The potential difference should be sufficient to cause, or assist in causing, fluid flow through the plural flow channels 59, which is based in part on the fluid characteristics of any particular application. As shown in FIG. 1, the potential source 68 may comprise a vacuum generator that is conventionally connected with a collector receptacle 70. The collector receptacle 70 is fluidically connected with the manifold 64 by way of a conventional flexible tube 66. Thus, by the provision of a vacuum at the source 68, a fluid or fluid mixture can be drawn from outside the separation module 55 through the separation media 62 and into the channels 59. The filtered fluid, or filtrate, then flows from the flow channels 59 out through the manifold 64 and through tube 66 into the collection receptacle 70. The receptacle 70 may advantageously be openable to permit the filtrate to be removed therefrom for other use and/or processing, or may be otherwise connected with conventional drainage systems or mechanisms.

In the case where the potential source 68 comprises a vacuum generator, the vacuum provided to the channels 59 via manifold 64 may be sufficient to adequately hold the separation media 62 against the structured surface 58. That is, the vacuum itself will tend to hold the separation media 62 against peaks 60 of the structured surface 58. Thus, the potential provided from an external source can be more effectively and efficiently distributed over the structured surface 58 of layer 57.

Other potential sources 68 are useable in accordance with the present invention instead of or in conjunction with a vacuum generation device. Generally, any manner of causing fluid flow through the channels 59 is contemplated except based purely on gravitational forces. That is, any external device that causes fluid to be transported through the channels 59 is contemplated. Examples of other potential sources include but are not limited to, vacuum pumps, pressure pumps and pressure systems, magnetic systems, magneto hydrodynamic drives, acoustic flow systems, centrifugal spinning and any other known or developed fluid drive system utilizing the creation of a potential difference that causes fluid flow to at least to some degree.

Figure 5:
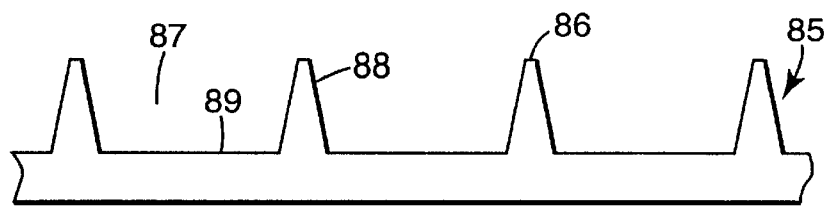
FIG. 5 is an end view of a structured layer illustrating another channel configuration in accordance with the present invention.
Figure 6:
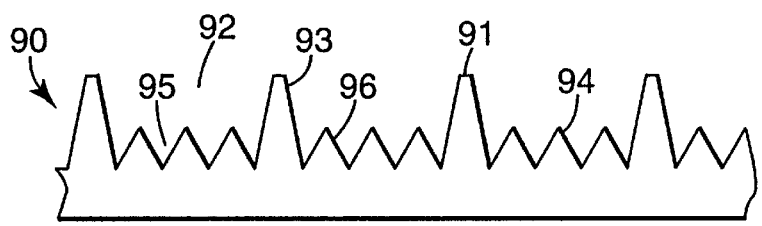
FIG. 6 is an end view of a structured layer illustrating yet another channel configuration in accordance with the present invention.

Although the embodiment of FIGS. 1, 2 and 4 is shown with structured surfaces 57 comprising multiple peaks 60 whose sidewalls 61 of each successive peak 60 converge to define a line at the base of the channel 59, other channel configurations are contemplated. A specific application for the separation device 50 may determine the number, type and size of the channels 59 provided to meet the separation requirements. For example in FIG. 5, the channels 87 are defined by a continuous series of peaks 86 which are separated by a wide, flat floor 89. Each peak 86 is flattened at the top, thereby facilitating bonding with an adjacent layer, such as the separation media 62. Each peak 86 could also be pointed, if desired. In FIG. 6, wide channels 92 are defined between peaks 91, but instead of providing a planar floor between channel sidewalls 93, a plurality of smaller sub-peaks 94 are provided. These sub-peaks 94 thus define secondary channels 95 therebetween. Sub-peaks 94 may or may not rise to the same level as peaks 91, and as illustrated, create a first wide channel 92 including smaller channels 95 distributed therein. The peaks 91 and sub-peaks 94 need not be evenly distributed with respect to themselves or each other. The smaller channels 95 can be used, for example, to control fluid flow through the wider channels 92.

Although FIGS. 1–6 contemplate elongated, linearly-configured channels, the channels may be provided in many other configurations. For example, the channels could have varying cross-sectional widths along the channel length; that is, the channels could diverge and/or converge along the length of the channel. The channel sidewalls could also be contoured rather than being straight in the direction of extension of the channel, or in the channel height. Generally, any channel configuration that can provide at least multiple discrete channel portions that extend from a first point to a second point within the separation device are contemplated.

Figure 7:
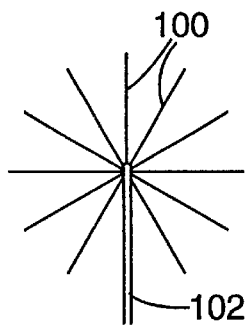
FIG. 7 is a top view of a structured layer illustrating one channel layout configuration in accordance with the present invention.
Figure 8:
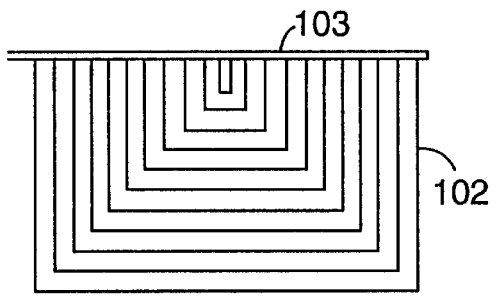
FIG. 8 is a top view of a structured layer illustrating another channel layout configuration in accordance with the present invention.
Figure 9:
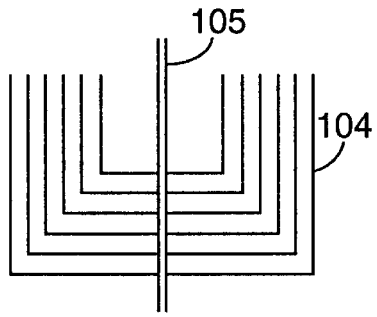
FIG. 9 is a top view of a structured layer illustrating yet another channel layout configuration in accordance with the present invention.

In FIG. 7, a channel configuration is illustrated in plan view that may be applied to the layer 57 to define the structured surface 58. As shown, plural converging channels 100 can be provided for intermediate collection of fluid and that are further connected with a single discrete channel 102. This minimizes the provision of outlet ports to one. As shown in FIGS. 8 and 9, a central channel 103 or 105 may be connected with a plurality of channel branches 102 or 104 that may be designed to cover a particular surface area of the structured surface for removing fluid from that particular area. Again, generally any pattern is contemplated in accordance with the present invention as long as a plurality of discrete channels are provided over a portion of the structured surface 58 from a first point to a second point. The aim of the channel pattern is to distribute the potential across the surface area of the separation media 62 in order to efficiently utilize the separation media 62 in separating constituents from a fluid mixture as it passes through the separation media 62.

As to any of the channels 59 contemplated above and in accordance with the present invention, such channels 59 are defined within layer 57 by the structured surface 58 of a first major surface of the layer 57. The channels in accordance with the present invention are configured to be discrete to allow any one channel to receive fluid from the ambient environment independently of the other channels. The microstructured size of each channel encourages single-phase flow. Without having air entrained in the liquid, noise generation is significantly reduced and less stress can be placed on liquids that are transported through the active fluid transport device.

The individual flow channels of the microstructured surfaces of the invention are substantially discrete. That is, fluid can move through the channels independent of fluid in adjacent channels. The channels independently accommodate the potential relative to one another to direct a fluid along or through a particular channel independent of adjacent channels. Preferably, fluid that enters one flow channel does not, to any significant degree, enter an adjacent channel, although there may be some diffusion between adjacent channels. It is important to effectively maintain the discreteness of the micro-channels in order to effectively transport the fluid and maintain advantages that such channels provide. Not all of the channels, however, may need to be discrete for all embodiments. Some channels may be discrete while others are not. Additionally, channel "discreteness" may be a temporary phenomenon driven, for example, by fluctuating pressures.

As used here, aspect ratio means the ratio of a channel's length to its hydraulic radius, and hydraulic radius is the wettable cross-sectional area of a channel divided by its wettable channel circumference. Preferably, the structured surface 58 is a microstructured surface that defines discrete flow channels that have a minimum aspect ratio (length/hydraulic radius) of 10:1, in some embodiments exceeding approximately 100:1, and in other embodiments at least about 1000:1. At the top end, the aspect ratio could be indefinitely high but generally would be less than about 1,000,000:1. The hydraulic radius of a channel is no greater than about 300 $\mu$m. In many embodiments, it can be less than 100 $\mu$m, and may be less than 10 $\mu$m. Although smaller is generally better for many applications (and the hydraulic radius could be submicron in size), the hydraulic radius typically would not be less than 1 $\mu$m for most embodiments. As more fully described below, channels defined within these parameters can provide efficient bulk fluid transport through an active fluid transport device.

The structured surface 58 can also be provided with a very low profile. Thus, active fluid transport devices are contemplated where the structured polymeric layer has a thickness of less than 5000 micrometers, and even possibly less than 1500 micrometers. To do this, the channels may be defined by peaks that have a height of approximately 5 to 1200 micrometers and that have a peak distance of about 10 to 2000 micrometers.

Microstructured surfaces in accordance with the present invention provide flow systems in which the volume of the system is highly distributed. That is, the fluid volume that passes through such flow systems is distributed over a large area. Microstructure channel density from about 10 per lineal cm (25/in) and up to one thousand per lineal cm (2500/in) (measured across the channels) provide for high fluid transport rates. Generally, when a common manifold is employed, each individual channel has an aspect ratio that is at least 400 percent greater, and more preferably is at least 900 percent greater than a manifold that is disposed at the channel inlets and outlets. This significant increase in aspect ratio distributes the potential's effect to contribute to the noted benefits of the invention.

Figure 10:
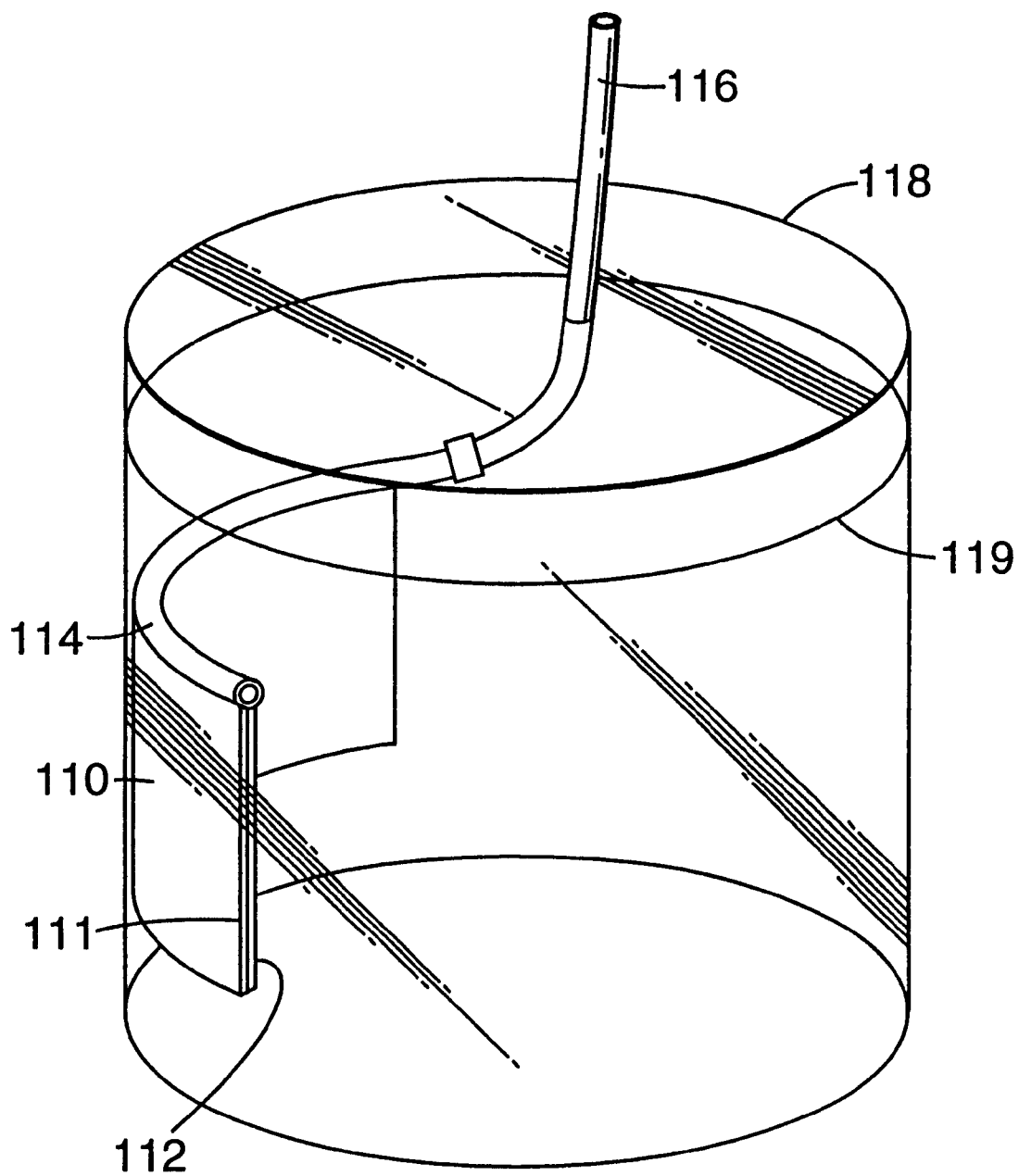
FIG. 10 is a perspective view of a separation module in accordance with the present invention submerged in a fluid mixture within a container.

FIG. 10 illustrates an embodiment of an immersible flexible separation module 110 in accordance with the present invention used to remove constituents from a fluid mixture 119 held in a container 118. The separation module 110 has a flexible structured layer 111 and a flexible separation media 112 coupled to a flexible manifold 114, thereby providing fluid connection between the flow channels (not shown) of the structured surface 111 and the manifold 114. Preferably, layers 111 and 112 are sealed together at all sides and to the manifold 114. Thus, the edges of the separation module 110 are closed so that flow of the fluid mixture 119 goes through the separation media 112, into the channels (not shown) of the structured layer 111, and out through the manifold 114. A flexible hose 116 connects the manifold 114 to an external source (not shown). A source, such as a vacuum, is provided to cause flow through the hose 116 and manifold 114, so that the fluid mixture 119 passes through the separation media 112 for removing constituent(s) from the fluid mixture 119. The filtered fluid then flows along the flow channels (not shown) of the structured layer 111 into the manifold 114 and out the hose 116 to a reservoir or other receptacle (not shown). By being flexible, the separation module 110 may conform to a surface of the container 118, such as a wall or floor, thereby improving the separation device's ability to efficiently perform the separation process. Being immersible, the separation module 110 may be submerged in any desired fluid mixture in order to facilitate effective constituent removal from the fluid mixture. In addition, the flat, large surface area of the module effectively uses the filter separation media's filtering capacity by spreading the intake of the fluid mixture across the entire surface area of the separation media. Although the separation module 110 need only be partially submerged, it is preferably completely submerged to most efficiently filter a bulk fluid mixture.

Figure 11:
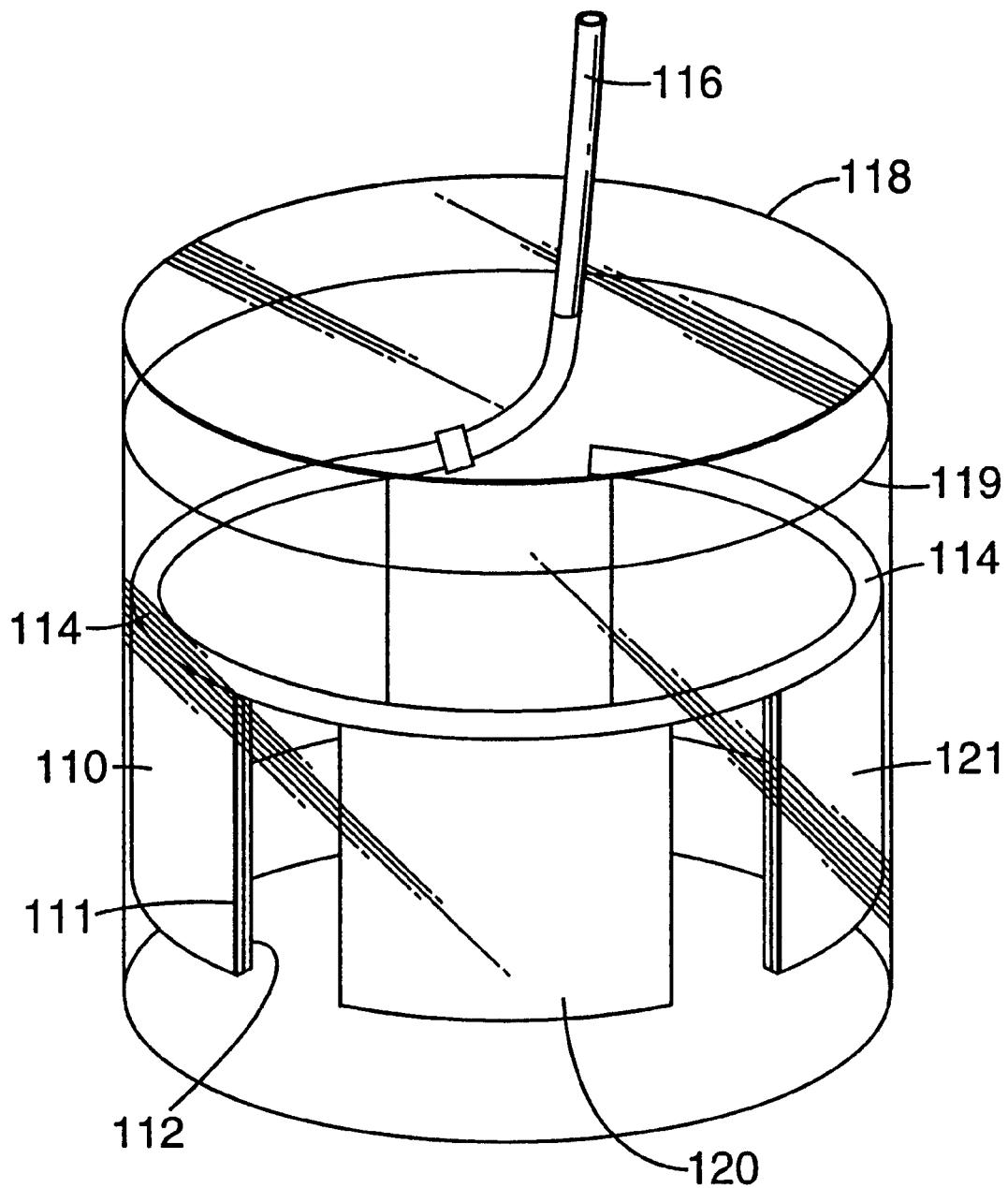
FIG. 11 is a perspective view of multiple separation modules having a common manifold in accordance with the present invention submerged in a fluid mixture within a container.

In order to increase the capacity of a separation device 50, the size of a separation module 110 could be increased. However, when size increases are limited due to container 118 size or configuration, a plurality of separation modules 110, 120 and 121 could be combined on a common manifold 114 to increase separation capacity instead, as illustrated in FIG. 11. Again, flexibility of the separation modules improves the separation device's ability to efficiently perform the separation process. In addition, a plurality of independent separation modules 110, that is separation modules having individual manifolds from a common source, or even individual separation modules having different sources, could also be employed in a single container 118, or a plurality of separation modules 110, 120, 121 on a common manifold could be placed in separate containers.

Another method of increasing separation capacity of a separation device 50 or separating more than one constituent from a fluid mixture, aside from increasing the number of layers of separation media 62 employed in the separation module 55, would be to pass a fluid mixture through a series of separation modules 55. These modules 55 may have different separation media 62 or they may have the same separation media 62, depending on the requirements of the separation process being performed. Various methods that are known or developed may be used to perform the separation process through a series of separation modules 55, including the use of a series of separation devices 50 wherein the separation module 55 of one is placed within the receptacle 70 of another.

Figure 12:
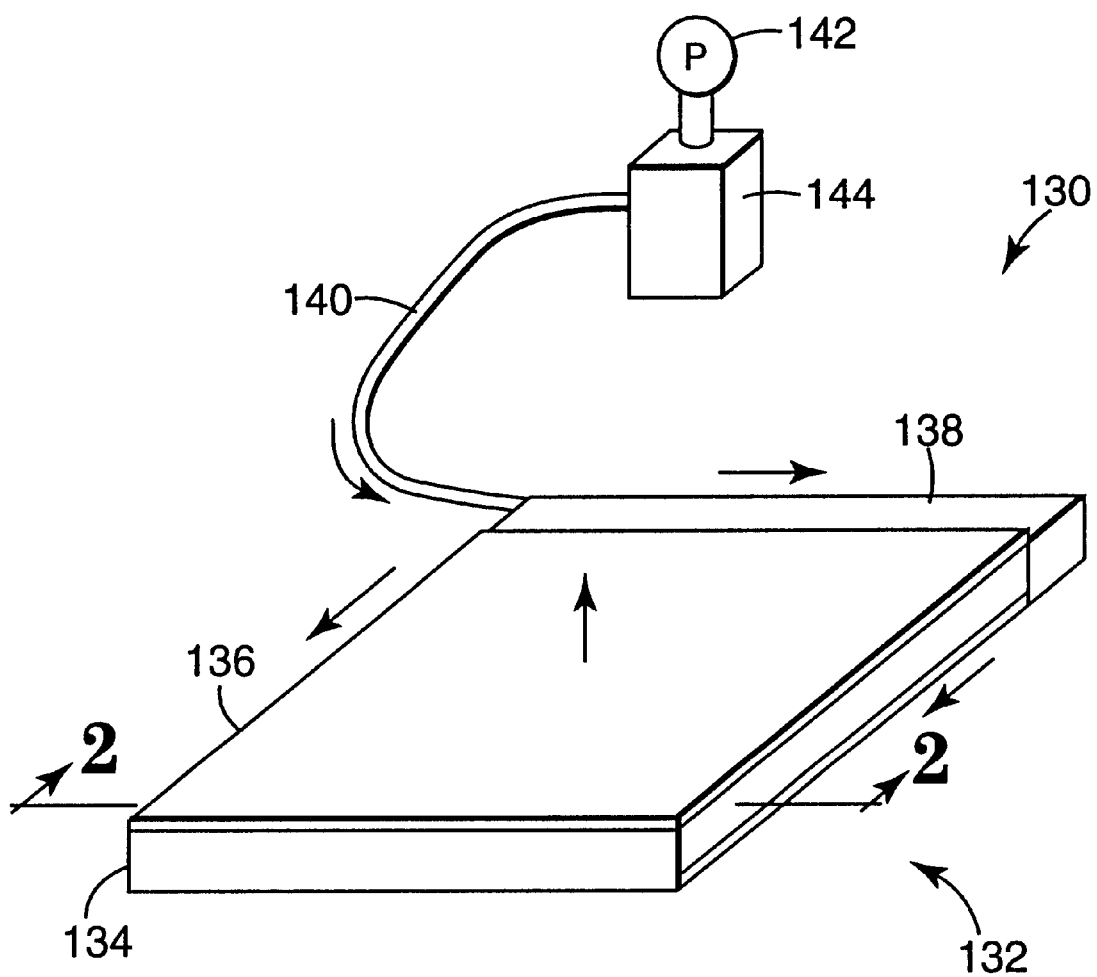
FIG. 12 is a perspective view of a separation device in accordance with the present invention using a pressure source to drive a fluid mixture.

An alternate embodiment of a separation device 130 of the present invention is shown in FIG. 12, wherein the source 142 comprises a pressure pump. In this embodiment, the pump 142 transports a fluid mixture from a reservoir 144 under pressure through a flexible hose 140 and into an internal chamber (not shown) of a manifold 138. From the manifold 138, the fluid mixture is transported through the flow channels (not shown) of the structured surface 134 of separation module 132, and then out through the separation media 136. The filtered fluid may be output from the separation module 132 into the environment, or into a container (not shown) or other suitable receptacle. For this embodiment, the cross-sectional view shown in FIG. 2, taken along line 2—2 of FIG. 12, also applies. Other channel configurations, as discussed above, may also be used in this present device. A separation device 130 of this embodiment could be used in conjunction with a separation device 50 of the prior embodiment, shown in FIG. 1, for performing a series of separations, or other processes. A separation device 130 of this embodiment may also be combined with one or more separation devices of the same or different embodiments, as required. The descriptions of the separation device components given above apply equally to the components of this device 130.

Another alternate embodiment of a separation device 150 in accordance with the present invention is illustrated in FIG. 13. This embodiment differs from the other embodiments previously described in that a source (not shown) provides a potential over the separation module 151 through a separation cover 160. The separation cover 160 defines a chamber (not shown) and preferably fully encloses the separation media 154 to provide fluid communication between the source and the separation media 154 of the separation module 151. An inlet 162 connects the internal chamber of the separation cover 160 to the source, preferably by way of a conduit (not shown). This separation module 151 also comprises a manifold 156 that is in fluid communication with the flow channels of the structured surface 152, in the same manner described above for other embodiments. In addition, an optional second manifold 158 is shown in fluid communication with the flow channels of the structured surface 154 on the opposite side of the separation module 151 than the first manifold 156.

When the source is a pressure source, a fluid mixture is provided from the source and flows through the inlet 162 into the internal chamber of the separation cover 160, and then through the separation media 154. The filtered fluid is transported from the separation media 154, through the flow channels of the structured surface 152, into the manifolds 156, 158, and out to a receptacle, the environment, or other suitable area. When the source is a vacuum source connected to the inlet 162 of the separation cover 160, a fluid mixture is pulled into the manifolds 156, 158 by suction from a suitable container, or the like. If no manifolds are provided, fluid mixture could enter one or all of one or more sides of the structured layer 152. The fluid mixture is then transported into the flow channels of the structured layer 152, and through the separation media 154. The filtered fluid then flows into the internal chamber of the separation cover 160 and out through the inlet 162 to a receptacle (not shown), or other suitable location. Alternatively, the vacuum source may be connected to the separation module 151 at the manifolds 156, 158, so that a fluid mixture is pulled from a reservoir (not shown) connected to the inlet 162 of the separation cover 160. The fluid mixture would then be transported into the internal chamber of the separation cover 160 and on into the flow channels of the structured layer 152, by way of the separation media 154. The filtered fluid would then flows into the manifold and out through a connecting conduit (not shown) to a receptacle (not shown), or other suitable location. As with the other embodiments of the present invention, this separation device 150 may be combined with one or more separation devices of the same or different embodiments. The descriptions of the separation device components given above apply equally to the components of this device 150.

The making of structured surfaces, and in particular microstructured surfaces, on a polymeric layer such as a polymeric film are disclosed in U.S. Pat. Nos. 5,069,403 and 5,133,516, both to Marentic et al. Structured layers may also be continuously microreplicated using the principles or steps described in U.S. Pat. No. 5,691,846 to Benson, Jr. et al. Other patents that describe microstructured surfaces include U.S. Pat. No. 5,514,120 to Johnston et al., U.S. Pat. No. 5,158,557 to Noreen et al., U.S. Pat. No. 5,175,030 to Lu et al., and U.S. Pat. No. 4,668,558 to Barber.

Structured polymeric layers produced in accordance with such techniques can be microreplicated. The provision of microreplicated structured layers is beneficial because the surfaces can be mass produced without substantial variation from product-to-product and without using relatively complicated processing techniques. "Microreplication" or "microreplicated" means the production of a microstructured surface through a process where the structured surface features retain an individual feature fidelity during manufacture, from product-to-product, that varies no more than about 50 µm. The microreplicated surfaces preferably are produced such that the structured surface features retain an individual feature fidelity during manufacture, from product-to-product, which varies no more than 25 µm.

In accordance with the present invention, a microstructured surface comprises a surface with a topography (the surface features of an object, place or region thereof) that has individual feature fidelity that is maintained with a resolution of between 50 micrometers and 0.05 micrometers, more preferably between 25 micrometers and 1 micrometer.

Structured layers for any of the embodiments in accordance with the present invention can be formed from a variety of polymers or copolymers including thermoplastic, thermoset, and curable polymers. As used here, thermoplastic, as differentiated from thermoset, refers to a polymer which softens and melts when exposed to heat and re-solidifies when cooled and can be melted and solidified through many cycles. A thermoset polymer, on the other hand, irreversibly solidifies when heated and cooled. A cured polymer system, in which polymer chains are interconnected or crosslinked, can be formed at room temperature through use of chemical agents or ionizing irradiation.

Polymers useful in forming a structured layer in articles of the invention include but are not limited to polyolefins such as polyethylene and polyethylene copolymers, polyvinylidene diflouride (PVDF), and polytetrafluoroethylene (PTFE). Other polymeric materials include acetates, cellulose ethers, polyvinyl alcohols, polysaccharides, polyolefins, polyesters, polyamids, poly(vinyl chloride), polyurethanes, polyureas, polycarbonates, and polystyrene. Structured layers can be cast from curable resin materials such as acrylates or epoxies and cured through free radical pathways promoted chemically, by exposure to heat, UV, or electron beam radiation.

As indicated above, there are applications where flexible active fluid transport devices are desired. Flexibility may be imparted to a structured polymeric layer using polymers described in U.S. Pat. No. 5,450,235 to Smith et al. and U.S. Pat. No. 5,691,846 to Benson, Jr. et al. The whole polymeric layer need not be made from a flexible polymeric material. A main portion of the polymeric layer, for example, could comprise a flexible polymer, whereas the structured portion or portion thereof could comprise a more rigid polymer. The patents cited in this paragraph describe use of polymers in this fashion to produce flexible products that have microstructured surfaces.

Polymeric materials including polymer blends can be modified through melt blending of plasticizing active agents such as surfactants or antimicrobial agents. Surface modification of the structured surfaces can be accomplished through vapor deposition or covalent grafting of functional moieties using ionizing radiation. Methods and techniques for graft-polymerization of monomers onto polypropylene, for example, by ionizing radiation are disclosed in U.S. Pat. Nos. 4,950,549 and 5,078,925. The polymers may also contain additives that impart various properties into the polymeric structured layer. For example, plasticisers can be added to decrease elastic modulus to improve flexibility.

Preferred embodiments of the invention may use thin flexible polymer films that have parallel linear topographies as the microstructure-bearing element. For purposes of this invention, a "film" is considered to be a thin (less than 5 mm thick) generally flexible sheet of polymeric material. The economic value in using inexpensive films with highly defined microstructure-bearing film surfaces is great. Flexible films can be used in combination with a wide range of separation media and can be used unsupported or in conjunction with a supporting body where desired. The microstructured surfaces may be flexible for many applications but also may be associated with a rigid structural body where applications warrant.

Because the devices of the invention include microstructured channels, the devices commonly employ a multitude of channels per device. As shown in some of the embodiments illustrated above, inventive devices can easily possess more than 10 or 100 channels per device. Some applications, the device may have more than 1,000 or 10,000 channels per device. The more channels that are connected to an individual potential source allow the potential's effect to be more highly distributed.

EXAMPLE

To determine the efficacy of an active fluid transport separation device having a plurality of discrete flow passages defined by a layer having microchannels in a microstructured surface and a separation media cover layer, a separation device was constructed using a separation module formed from a microstructure-bearing film element, capped with a separation media. The microstructure-bearing film was formed by casting a molten polymer onto a microstructured nickel tool to form a continuous film with channels on one surface. The channels were formed in the continuous length of the cast film. The nickel casting tool was produced by shaping a smooth copper surface with diamond scoring tools to produce the desired structure followed by an electroless nickel plating step to form a nickel tool. The tool used to form the film produced a microstructured surface with abutted 'V' channels with a nominal depth of 459 µm and an opening width of 420 µm. This resulted in a channel, if closed, with a mean hydraulic radius of 62.5 µm. The polymer used to form the film was low density polyethylene, Tenite™ 1550P from Eastman Chemical Company. A nonionic surfactant, Triton X-102 from Rohm & Haas Company, was melt blended into the base polymer to increase the surface energy of the film.

The separation media was a nonwoven blown microfiber web. The nonwoven web was produced from polypropylene, Fina 100 MFI, and had a solidity of 8% with fibers in the 2–5 Tm diameter size and a basis weight of 50 g/m². Capping of the microreplicated film was accomplished by layering the film and nonwoven together with the microstructure of the film facing the nonwoven. After layering, the composite was sealed on the two sides parallel to the linear microstructure. One end of the composite, where the microchannels terminated, was also heat sealed. The unsealed end was attached to the manifold that extended the width of the module.

The manifold was formed by placing a cut in the side wall of a section of tubing, VI grade 3.18 mm inner diameter, 1.6 mm wall thickness tubing form Nalge Co. of Rochester, N.Y. The slit was cut with a razor in a straight line along the axis of the tube. The length of the slit was approximately the width of the module. The tube was then fitted over the end of the module and hot met glued in place. One open end of the tube, at the module, was sealed closed with hot melt adhesive. The dimension of the module was 80 mm×120 mm.

To evaluate the liquid/solid separation capability of the test module the unit was placed in a beaker with water and fine particle solids of AC test Dust, SAE coarse, commercially available from Powder Technology Inc. The test was conducted with the test unit placed in a 500 ml beaker, with the film side of the unit flat next to the inside wall of the beaker. A liquid recovery flask with a vacuum source was then attached to the test unit. After the vacuum was established, the beaker was filled to the top, submerging the test unit, with a suspension of AC test dust in water at a concentration of 15 g/1000 ml. Liquid in the beaker was removed, through the separation module, to the recovery flask as the AC dust suspension was constantly stirred in the beaker. After the liquid was extracted through the microstructure-bearing film based separation apparatus, the recovered liquid was observed for the presence of suspended matter. No suspended matter was observed in the recovered liquid.

While a single microstructure-bearing film based separation module was used in the evaluation, multiple units could be used to increase separation capacity. A separation device of this kind, with the appropriate separation media, could be used in other separation applications such as air filtration. For very fine separations, a microporous film, for example, might be employed as the separation media. An alternate design might utilize a supplied fluid, passing first within a separation module, whereby the fluid flowing through the channels would exchange with the environment through the separation medium.

While the example unit was used to demonstrate a liquid/solid separation, other separations could also be accomplished with the use of similar constructions. Other separation mediums could be used as the application requires. Microporous membranes, for instance, would be particularly suited to applications where gas/gas or ultrafine solid/liquid separations are required.

All of the patents and patent applications cited above are wholly incorporated by reference into this document. Also, this application also wholly incorporates by reference the following patent applications that are commonly owned by the assignee of the subject application and filed on even date herewith: U.S. patent application Ser. No. 09/099,269, to Insley et al. and entitled "Microchanneled Active Fluid Transport Devices"; U.S. patent application Ser. No. 09/106,506, to Insley et al. and entitled "Structured Surface Filtration Media"; U.S. patent application Ser. No. 09/099,632, to Insley et al. and entitled "Microchanneled Active Fluid Heat Exchanger"; and U.S. patent application Ser. No. 09/099,565, to Insley et al. and entitled "Fluid Guide Device Having an Open Microstructured Surface for Attachment to a Fluid Transport Device."

Although the present invention has been described with reference to preferred embodiments, workers skilled in the art will recognize that changes may be made in form and detail without departing from the spirit and scope of the invention.

What is claimed is:

1. An active fluid transport separation device for removing a constituent from a fluid mixture to produce a fluid component, the active fluid transport device comprising:

a substantially impermeable first layer including a polymeric flexible film having first and second major surfaces, wherein the first major surface is defined by a structured surface formed within the first layer, the structured surface having a plurality of flow channels along the surface of the first layer, the flow channels each having a minimum aspect ratio of about 10:1 and a hydraulic radius no greater than about 300 micrometers;

a selectively permeable fluid separation medium having first and second major surfaces, the first major surface overlying and in contact with at least a portion of the first major surface of the first layer and covering a plurality of the flow channels, and wherein the second major surface is substantially free of microchanneled structure; and a source external to the structured surface, the source providing at least one of a first potential and a second potential distributed over the flow channels, promoting movement of only the fluid component from the first potential through the selectively permeable fluid separation medium into a plurality of the flow channels, and along the plurality of flow channels to the second potential.

2. The active fluid transport separation device of claim 1, further comprising a manifold in fluid communication with the flow channels and connected at a common end to at least two of the flow channels for operatively permitting the source to provide the potential distributed over the flow channels.

3. The active fluid transport separation device of claim 2, wherein the source comprises a vacuum generator that is operatively connected to the manifold.

4. The active fluid transport separation device of claim 2, wherein the source provides the fluid mixture under pressure.

5. The active fluid transport separation device of claim 1, wherein the selectively permeable fluid separation medium comprises separation material selected from the group consisting of microporous film, nonwoven filtration web, and micro-perforated film.

6. The active fluid transport separation device of claim 5, wherein the selectively permeable fluid separation medium comprises a plurality of separation material layers.

7. The active fluid transport separation device of claim 6, wherein at least one of the separation media layers comprises a different selectively permeable separation material than another.

8. The active fluid transport separation device of claim 1, wherein the plurality of flow channels are defined by a series of peaks, each peak having two sidewalls.

9. The active fluid transport separation device of claim 8, wherein the sidewalls of adjacent peaks of the flow channels are separated by a planar floor.

10. The active fluid transport separation device of claim 8, wherein the flow channels of a structured polymeric surface each comprise a cross-sectional characteristic, the cross-sectional characteristic of at least a portion of a flow channel being varied across the structured polymeric surface.

11. The active fluid transport separation device of claim 8, wherein one flow channel of a structured polymeric surface is configured differently from another flow channel thereof.

12. The active fluid transport separation device of claim 1, further comprising:

at least one additional layer of polymeric film material having first and second major surfaces, wherein the first major surface is defined by a structured surface formed within the additional layer, the structured surface having a plurality of flow channels along the surface of the additional layer, the flow channels each having a minimum aspect ratio of about 10:1 and a hydraulic radius no greater than about 300 micrometers;

a second selectively permeable fluid separation medium having first and second major surfaces, the first major surface overlying and in contact with at least a portion of the first major surface of the additional layer and covering a plurality of the flow channels of the additional layer, and wherein the second major surface is substantially free of microchanneled structure; and wherein the external source provides at least one of a first potential and a second potential distributed over the flow channels of the additional layer, promoting movement of only the fluid component from the first potential through the second selectivetly permeable fluid separation medium into a plurality of the flow channels of the additional layer, and along the plurality of flow channels of the additional layer to the second potential.

13. The active fluid transport separation device of claim 12, further comprising a manifold in fluid communication with the flow channels of the first layer and the additional layer and connected to at least one of the flow channels of the structured surface of the first layer and at least one of the flow channels of the additional layer for operatively permitting the source to provide a potential over the flow channels of both the first and the additional layers.

14. An active fluid transport separation device for removing a constituent from a fluid mixture to produce a fluid component, the active fluid transport device comprising:

a substantially impermeable first layer including a polymeric flexible film having first and second major surfaces, wherein the first major surface is defined by a structured surface formed within the first layer, the structured surface having a plurality of flow channels along the surface of the first layer, wherein the plurality of flow channels are defined by a series of peaks, each peak having two sidewalls, and wherein the sidewalls of adjacent peaks of the flow channels are separated by at least one sub-peak, the sub-peak defining a plurality of sub-channels within each flow channel, the flow channels each having a minimum aspect ratio of about 10:1 and a hydraulic radius no greater than about 300 micrometers;

a selectively permeable fluid separation medium having first and second major surfaces, the first major surface overlying and in contact with at least a portion of the first major surface of the first layer and covering a plurality of the flow channels, and wherein the second major surface is substantially free of microchanneled structure; and a source external to the structured surface, the source providing at least one of a first potential and a second potential distributed over the flow channels, promoting movement of only the fluid component from the first potential through the selectively permeable fluid separation medium into a plurality of the flow channels, and along the plurality of flow channels to the second potential.

15. A method of removing a constituent of a fluid mixture to produce a fluid component, comprising the steps of:

(a) providing a separation module having a substantially impermeable first layer including a polymeric flexible film having first and second major surfaces, wherein the first major surface is defined by a structured surface formed within the first layer, the structured surface having a plurality of flow channels along the surface of the first layer, the flow channels each having a minimum aspect ratio of about 10:1 and a hydraulic radius no greater than about 300 micrometers, and a selectively permeable fluid separation medium having first and second major surfaces, the first major surface overlying and in contact with at least a portion of the first major surface of the first layer and covering a plurality of the flow channels, and wherein the second major surface is substantially free of microchanneled structure;

(b) providing a fluid mixture having a constituent;

(c) connecting the separation module to a source provided external to the structured surface, for providing at least one of a first potential and a second potential distributed over the flow channels;

(d) exposing the fluid mixture to the separation medium;

(e) passing only the fluid component from the first potential through the selectively permeable fluid separation medium into a plurality of the flow channels; and (f) transporting the fluid component along the flow channels to the second potential by action of the external source.

16. The method of claim 15, wherein the externally provided source is a vacuum generator.

17. The method of claim 15, wherein the externally provided source provides the fluid mixture under pressure.

18. The method of claim 15, wherein the selectively permeable fluid separation medium comprises a plurality of separation material layers.

19. The method of claim 18, wherein at least one of the separation material layers comprises a different separation material than another separation material layer.

* * * * *

UNITED STATES PATENT AND TRADEMARK OFFICE
CERTIFICATE OF CORRECTION

PATENT NO.    : 6,514,412 B1
DATED         : February 4, 2003
INVENTOR(S)   : Insley, Thomas I.

It is certified that error appears in the above-identified patent and that said Letters Patent is hereby corrected as shown below:

<u>Title page,</u>
Item [56], References Cited, U.S. PATENT DOCUMENTS, please add:

| | | |
|---|---|---|
| 3,234,639 | 2/1966 | Dietzsch |
| 3,520,300 | 7/1970 | Flower, Jr. |
| 3,715,192 | 2/1973 | Wenz et al. |
| 3,812,972 | 5/1974 | Rosenblum |
| 3,935,863 | 2/1976 | Kliger |
| 3,993,566 | 11/1976 | Goldberg et al. |
| 4,233,029 | 11/1980 | Columbus |
| 4,271,119 | 6/1981 | Columbus |
| 4,277,966 | 7/1981 | Rambauske |
| 4,533,352 | 8/1985 | Van Beek et al. |
| 4,668,558 | 5/1987 | Barber |
| 4,677,705 | 7/1987 | Schuster |
| 4,679,590 | 7/1987 | Hergenroeder |
| 4,747,166 | 5/1988 | Kuntz |
| 4,751,000 | 6/1988 | Drori |
| 4,906,439 | 3/1990 | Grenner |
| 4,950,549 | 8/1990 | Rolando et al. |
| 4,978,450 | 12/1990 | Drori |
| 5,014,389 | 5/1991 | Ogilvie et al. |
| 5,037,548 | 8/1991 | Rosenberg |
| 5,069,403 | 12/1991 | Marentic et al. |
| 5,078,925 | 1/1992 | Rolando et al. |
| 5,133,516 | 7/1992 | Marentic et al. |
| 5,158,557 | 10/1992 | Noreen et al. |
| 5,175,030 | 12/1992 | Lu et al. |
| 5,200,248 | 4/1993 | Thompson et al. |
| 5,249,359 | 10/1993 | Schubert et al. |
| 5,349,965 | 9/1994 | McCarver |
| 5,437,651 | 8/1995 | Todd et al. |
| 5,440,332 | 8/1995 | Good |
| 5,445,771 | 8/1995 | Degen |
| 5,450,235 | 9/1995 | Smith et al. |
| 5,457,848 | 10/1995 | Miwa |
| 5,534,576 | 7/1996 | Grot |
| 5,599,330 | 2/1997 | Rainin |
| 5,628,735 | 5/1997 | Skow |
| 5,651,888 | 7/1997 | Shimizu et al. |
| 5,655,258 | 8/1997 | Heintz |

UNITED STATES PATENT AND TRADEMARK OFFICE
CERTIFICATE OF CORRECTION

PATENT NO.   : 6,514,412 B1
DATED        : February 4, 2003
INVENTOR(S)  : Insley, Thomas I.

It is certified that error appears in the above-identified patent and that said Letters Patent is hereby corrected as shown below:

Title page (cont'd),

| | | |
|---|---|---|
| 5,691,846 | 11/1997 | Benson Jr. et al. |
| 5,692,263 | 12/1997 | Sorenson |
| 5,728,446 | 3/1998  | Johnston et al. |
| 5,797,978 | 8/1998  | Rosenberg et al. |
| 5,842,787 | 12/1998 | Kopf-Sill et al. |
| 5,885,470 | 3/1999  | Parce et al. |
| 5,932,315 | 8/1999  | Lum et al. |

FOREIGN PATENT DOCUMENTS, please add:

| | | |
|---|---|---|
| DE | 42 10 072 A1   | 3/1993 |
| EP | 0 547 496 A1   | 12/1992 |
| GB | 1 418 635      | 12/1975 |
| WO | 89/04628       | 6/1989 |
| WO | 93/11727       | 6/1993 |
| WO | 99/06589       | 2/1999 |

OTHER PUBLICATIONS, please add:

Article: "Fabrication of Novel Three-Dimensional Microstructures by the Anisotropic Etching of (100) and (110) Silicon", Ernest Bassous, IEEE Transaction on Electron Devices, Vol. ED-25, No. 10, October 1978

Article: "Microtechnology Opens Doors to the Universe of Small Space", Peter Zuska Medical Device & Diagnostic Industry, January 1997

Article: "Simple and Low Cost Fabrication of Embedded Micro-Channels by Using a New Thick-Film Photoplastic", Guerin et al.; Digest of Technical Papers, Vol. 2, June 1997

Article: "Fabrication of Microstructures with high aspect ratios and great structural heights by synchrotron radiation lithography, galvanoforming, and plastic moulding (LIGA process)", Becker et al.; Microelectronic Engineering 4 (1986)

UNITED STATES PATENT AND TRADEMARK OFFICE
CERTIFICATE OF CORRECTION

PATENT NO. : 6,514,412 B1
DATED : February 4, 2003
INVENTOR(S) : Insley, Thomas I.

It is certified that error appears in the above-identified patent and that said Letters Patent is hereby corrected as shown below:

<u>Title page (cont'd),</u>

Article: "UV Laser Machined Polymer Substrates for the Development of Microdiagnostic System", Roberts et al.; <u>Analytical Chemistry</u>, Vol. 69, No. 11, June 1997
    Article: "Processing of Three-Dimensional Microstructures Using Macroporous n-Type Silicon", Ottow et al.; <u>J. Electrochem Soc.</u>, Vol. 143, No. 1, January 1996
    Product Literature: Technol Medical Products, Inc., "FLUID-CONTROL" Floor Mat Signed and Sealed this Sixth Day of April, 2004

JON W. DUDAS
*Acting Director of the United States Patent and Trademark Office*